United States Patent
Kim et al.

(10) Patent No.: US 11,591,531 B2
(45) Date of Patent: Feb. 28, 2023

(54) CONVERSION OF CATALYTIC COKE INTO SYNTHETIC GAS FROM A FLUID CATALYTIC CRACKING (FCC) PROCESS USING A CHEMICAL LOOPING SYSTEM AND METHODS RELATED THERETO

(71) Applicant: ExxonMobil Technology and Engineering Company, Annandale, NJ (US)

(72) Inventors: Hyung Rae Kim, Basking Ridge, NJ (US); Arun K. Sharma, Hellertown, PA (US); Bing Du, Pittstown, NJ (US)

(73) Assignee: ExxonMobil Technology and Engineering Company, Annandale, NJ (US)

( * ) Notice: Subject to any disclaimer, the term of this patent is extended or adjusted under 35 U.S.C. 154(b) by 265 days.

(21) Appl. No.: 16/947,874

(22) Filed: Aug. 21, 2020

(65) Prior Publication Data
US 2022/0056357 A1    Feb. 24, 2022

(51) Int. Cl.
*C10J 3/84* (2006.01)
*B01J 8/38* (2006.01)
(Continued)

(52) U.S. Cl.
CPC .............. *C10J 3/84* (2013.01); *B01J 8/1881* (2013.01); *B01J 8/24* (2013.01); *B01J 8/388* (2013.01); *C01B 3/48* (2013.01); *C01B 32/50* (2017.08); *C07C 29/1518* (2013.01); *C10G 11/18* (2013.01); *C10J 3/463* (2013.01); *B01J 2208/00548* (2013.01); *C01B 2203/0255* (2013.01); *C01B 2203/0283* (2013.01); *C01B 2203/86* (2013.01); *C10G 2300/4043* (2013.01); *C10G 2300/4081* (2013.01);
(Continued)

(58) Field of Classification Search
CPC ...... C10J 3/84; C10J 3/463; C10J 2300/0943; C10J 2300/1612; C10J 2300/1665; C10J 2300/1807; C10J 2300/0976; C10J 3/725; B01J 8/1881; B01J 8/24; B01J 8/388; B01J 2208/00548; C07C 29/1518; C01B 3/48; C01B 32/50; C01B 2203/0255; C01B 2203/0283; C01B 2203/86; C01B 2203/0415; C01B 2203/06; C10G 11/18; C10G 2300/4043; C10G 2300/4081; C10G 11/182; C10K 3/04

See application file for complete search history.

(56) References Cited

U.S. PATENT DOCUMENTS

| | | |
|---|---|---|
| 2,602,809 A | 7/1952 | Dickinson |
| 4,272,399 A | 6/1981 | Davis et al. |

(Continued)

*Primary Examiner* — Steven J Bos
*Assistant Examiner* — Syed T Iqbal
(74) *Attorney, Agent, or Firm* — Vorys, Sater, Seymour and Pease LLP (57) ABSTRACT

Provided is a process capable of converting the cokes on spent catalysts in a fluid catalytic cracking (FCC) process into synthesis gas. The produced synthesis gas contains high concentrations of CO and H$_2$ and may be utilized in many downstream applications such as syngas fermentation for alcohol production, hydrogen production and synthesis of chemical intermediates. A reducer/regenerator reactor for a fluid catalytic process comprising a chemical looping system to produce synthesis gas is also described.

24 Claims, 4 Drawing Sheets

(51) Int. Cl.
*B01J 8/18* (2006.01)
*C01B 3/48* (2006.01)
*C01B 32/50* (2017.01)
*C07C 29/151* (2006.01)
*C10G 11/18* (2006.01)
*C10J 3/46* (2006.01)
*B01J 8/24* (2006.01)

(52) U.S. Cl.
CPC .................. *C10J 2300/0943* (2013.01); *C10J 2300/1612* (2013.01); *C10J 2300/1665* (2013.01); *C10J 2300/1807* (2013.01)

(56) References Cited

U.S. PATENT DOCUMENTS

| 8,916,128 | B2 | 12/2014 | Hoteit et al. | |
| 2007/0232843 | A1* | 10/2007 | Beech | B01J 8/1827 422/147 |

* cited by examiner

CONVERSION OF CATALYTIC COKE INTO SYNTHETIC GAS FROM A FLUID CATALYTIC CRACKING (FCC) PROCESS USING A CHEMICAL LOOPING SYSTEM AND METHODS RELATED THERETO

FIELD OF THE INVENTION

This application relates to processes and systems for generating synthesis gas from catalyst coke generated by a fluid catalytic cracking process.

BACKGROUND OF THE INVENTION

Synthesis gas, a mixture containing carbon monoxide and hydrogen, is an important feedstock used in many industries to produce a wide range of chemicals. It is also known as a biofuel for use in hydrogen fuel cells. Synthesis gas is typically produced from coal, biomass or solid waste. Coal and heavy hydrocarbons may be gasified to produce synthesis gas. Light hydrocarbons may be reformed in the presence of steam, oxygen and/or carbon dioxide to also produce synthesis gas.

The fluid catalytic cracking (FCC) process is a common process used in petroleum refineries to convert high molecular weight hydrocarbons from crude oil to lower molecular weight hydrocarbons for use in gasoline, olefins and other hydrocarbon products. This conversion to lower molecular weight hydrocarbons is called cracking. The fluid catalytic cracking unit usually comprises a FCC reactor and a FCC regenerator. The feedstock for the FCC process is the portion of the crude oil typically with a boiling point greater than 340° C. (644° F.). This portion of the crude oil is typically preheated to a temperature of about 315 to 430° C., fed into the FCC reactor and then brought into contact with a catalyst to break down or "crack" the high molecular weight hydrocarbons. The FCC catalyst generally is a microspheroidal catalyst, which behaves like a liquid when aerated by gas. Typically, FCC catalysts are in the form of fine powders with an average particle size of 60-75 µm and a size distribution from 20 to 120 µm. When this catalytic cracking occurs, carbon-containing compounds (also known as catalyst coke) deposit in the pores of the FCC catalyst. The presence of catalyst coke generally reduces the activity of the FCC catalyst.

After the catalytic cracking occurs, the catalyst particles are separated from the cracked vapors. The spent catalyst particles are fed into a FCC regenerator. Typically, the spent catalyst particles contain between 0.4 to 2.5 wt % catalyst coke. The coke is composed of carbon, hydrogen and trace amounts of sulfur and nitrogen. In the FCC regenerator, a stream of air reacts with the catalyst coke particles to regenerate the catalyst. This combustion process in the FCC regenerator typically produces a large amount of $CO_2$ emissions in a petroleum refinery.

One method for reducing $CO_2$ emissions from the FCC regenerator is to reduce the amount of catalyst coke particles that generate the $CO_2$ emissions.

Another method for capturing $CO_2$ emissions and thereby decreasing $CO_2$ emissions to the environment is the chemical looping process. The chemical looping process utilizes oxygen carrier particles to convert carbon-based fuels to electricity, hydrogen and sequestrable $CO_2$. The oxygen carrier particles in the carbon looping process generally are metal oxides capable of undergoing a reduction reaction with the fuel stream and an oxidation reaction with an oxygen carrying stream. The reduction of the metal oxide particles with a carbon-based fuel typically generates streams of carbon monoxide, hydrogen, carbon dioxide, water vapor and reduced metal oxide particles. The reduced metal oxide particles are usually then oxidized with air to produce heat and/or oxidized with steam to produce hydrogen. These two reduction and oxidation reactions together is called the chemical looping process.

U.S. Pat. No. 2,602,809 discloses a method of producing synthesis gas where carbon monoxide is produced in one reactor, hydrogen is produced in another reactor and then combined in a separate reactor to produce synthesis gas.

U.S. Pat. No. 4,272,399 discloses carbon-containing materials that are gasified to produce synthesis gas, a mixture of hydrogen and carbon monoxide, in a three zone unified system (oxidizer, reducer and gasifier) using a metal oxide as the oxygen source.

U.S. Pat. No. 8,916,128 discloses a method of producing synthesis gas comprising an air-supplied oxidation reaction zone, a reduction reaction zone and gasification reaction zone in at least one chemical loop. Synthesis gas in U.S. Pat. No. 8,916,128 is produced in the gasification reaction zone using reduced metallic oxides.

There is a need to reduce $CO_2$ emissions from a FCC process. There is also a need to produce synthesis gas from a FCC process.

SUMMARY

Disclosed is a method for producing synthesis gas from catalyst coke generated from a fluid catalytic cracking process by
a) providing a chemical looping system comprising a reducer/regenerator reactor, an oxidizer reactor and a combustor reactor;
b) feeding catalyst coke particles and metal oxide particles into the reducer/regenerator reactor of the chemical looping system to produce a plurality of streams comprising a regenerated catalyst stream, a synthesis gas stream and a reduced metal oxide particle stream;
c) feeding the stream of reduced metal oxide particles and a stream of water vapor into the oxidizer reactor of the chemical looping system to produce a plurality of streams comprising a hydrogen stream and a stream of oxidized metal oxide particles; and
d) feeding the stream of oxidized metal oxide particles and a stream of air into the combustor reactor of the chemical looping system to produce heat and a stream of metal oxide particles.

Further disclosed is a method of reducing $CO_2$ emissions in a fluid catalytic cracking process by converting catalyst coke into synthesis gas by
a) providing a chemical looping system comprising a reducer/regenerator reactor, an oxidizer reactor and a combustor reactor;
b) feeding catalyst coke particles and metal oxide particles into the reducer/regenerator reactor of the chemical looping system to produce a plurality of streams comprising a regenerated catalyst stream, a synthesis gas stream and a reduced metal oxide particle stream;
c) feeding the stream of reduced metal oxide particles and a stream of water vapor into the oxidizer reactor of the chemical looping system to produce a plurality of streams comprising a hydrogen stream and a stream of oxidized metal oxide particles; and d) feeding the stream of oxidized metal oxide particles and a stream of air into the combustor reactor of the chemical looping system to produce heat and a stream of metal oxide particles.

BRIEF DESCRIPTION OF THE FIGURES

For a better understanding of the nature, objects, and processes involved in this disclosure, reference should be made to the detailed description taken in conjunction with the accompanying figures. The subject matter disclosed is capable of considerable modifications, alterations, combinations, and equivalents in form and function, as will occur to those skilled in the art and having the benefit of this disclosure.

DETAILED DESCRIPTION

As used herein, "wt %" means percentage by weight, "vol %" means percentage by volume, "mol %" means percentage by mole, "ppm" means parts per million. All "ppm" as used herein are ppm by weight unless specified otherwise. All concentrations herein are expressed on the basis of the total amount of the composition in question. All ranges expressed herein should include both end points as two specific embodiments unless specified or indicated to the contrary.

As used herein, the term "catalyst coke" or "coke" refers to carbon-containing compounds that deposit in the pores of the FCC catalyst during the fluid catalytic cracking process. Typically, the coke compounds are composed of carbon, hydrogen and trace amounts of sulfur and nitrogen. As used herein, the term "cokes" refer to a plurality of carbon-containing compounds that deposit in the pores of the FCC catalyst during the fluid catalytic cracking process.

As used herein, "feedstock" and "feed" (and grammatical derivatives thereof) are used interchangeably and both refer to a composition that is fed into a reactor. A feedstock may optionally have been pre-treated to modify its disposition.

As used herein, the term "hydrocarbon" refers to a class of compounds containing hydrogen bound to carbon, and encompasses (i) saturated hydrocarbon compounds; (ii) unsaturated hydrocarbon compounds; and (iii) mixtures of hydrocarbon compounds (saturated and/or unsaturated), including mixtures of hydrocarbon compounds having different values of n, i.e. differing carbon numbers.

As used herein, the term "metal oxide" refers to metal oxides comprising oxides, hydroxides, oxyhydroxides, and hydrated oxides of Al, Cu, Fe, Mg, Mn, Ni, and Ti. Exemplary metal oxide particles comprise copper oxide, nickel oxide, magnesium oxide, iron oxide, manganese oxide, titanium dioxide and/or mixtures thereof.

As used herein, the term "reactor" refers to any vessel(s) in which a chemical reaction occurs. Reactor includes both distinct reactors, as well as reaction zones within a single reactor apparatus and, as applicable, reactions zones across multiple reactors. For example, a single reactor may have multiple reaction zones. Where the description refers to a first and second reactor, the person of ordinary skill in the art will readily recognize such reference includes two reactors, as well as a single reactor vessel having first and second reaction zones. Likewise, a first reactor effluent and a second reactor effluent will be recognized to include the effluent from the first reaction zone and the second reaction zone of a single reactor, respectively.

As used herein, the term "synthesis gas" or "syngas" is a gas stream containing carbon monoxide and hydrogen.

In a Fluid Catalytic Cracking (FCC) process, high molecular weight hydrocarbons from crude oil are converted to lower molecular weight hydrocarbons. The fluid catalytic cracking unit usually comprises a FCC reactor and a FCC regenerator. The feedstock for the FCC process is the portion of the crude oil with a boiling point greater than 340° C. (644° F.). This portion of the crude oil is preheated to a temperature of about 315 to 430° C., fed into the riser and then into the FCC reactor and then brought into contact with a catalyst to break down or "crack" the high molecular weight hydrocarbons. The FCC catalyst is a microspheroidal catalyst, which behaves like a liquid when aerated by gas. Typically, FCC catalysts are in the form of fine powders with an average particle size of 60-75 μm and a size distribution from 20 to 120 μm. When this catalytic cracking occurs, carbon-containing compounds (also known as catalyst coke) deposit in the pores of the FCC catalyst. The presence of catalyst coke reduces the activity of the FCC catalyst.

After the catalytic cracking occurs, the catalyst particles are separated from the cracked vapors in the stripper. The spent catalyst particles are fed into a FCC regenerator. Typically, the spent catalyst particles contain between 0.4 to 2.5 wt % catalyst coke. The coke is composed of carbon, hydrogen and trace amounts of sulfur and nitrogen. In the FCC regenerator, a stream of air reacts with the catalyst coke to regenerate the catalyst. This combustion process in the FCC regenerator produces a large amount of $CO_2$ emissions in a petroleum refinery. As a result, the Fluid Catalytic Cracking (FCC) process is called one of largest $CO_2$ emissions source in a refinery.

To reduce the $CO_2$ emissions from the FCC process while regenerating the FCC catalyst, the present invention proposes a novel process for converting catalyst coke on the spent FCC catalysts into synthesis gas. The produced syngas from this process contains high concentrations of CO and $H_2$ which has the potential to be readily utilized in many downstream applications. Exemplary uses of synthesis gas are syngas fermentation for alcohol production, hydrogen production and synthesis of chemical intermediates. In the present invention, metal oxide particles (such as iron oxide) are directly processed with the spent FCC catalysts in a newly designed fluidized bed or co-current moving bed to convert the catalyst coke into syngas with high concentrations of CO and $H_2$. While the syngas is generated from the spent catalyst, the iron particles are reduced to a lower oxidation state. Later in the chemical looping process, the reduced iron particles can be used generate valuable products for the refinery such as $H_2$ and heat.

Direct Conversion of Catalyst Coke by Metal Oxide in Chemical Looping Process for CO Generation The re-designed FCC process concept incorporates a chemical looping process that utilizes as a metal oxide-based oxygen carrier to convert catalyst coke to products such as $H_2$, syngas and heat. Various metal oxides, for example, Cu, Ni, Mg, and Mn, are candidates for the oxygen carrier in the Chemical Looping process. Iron oxide is an example of metal oxide-based oxygen carrier.

Figure 1:
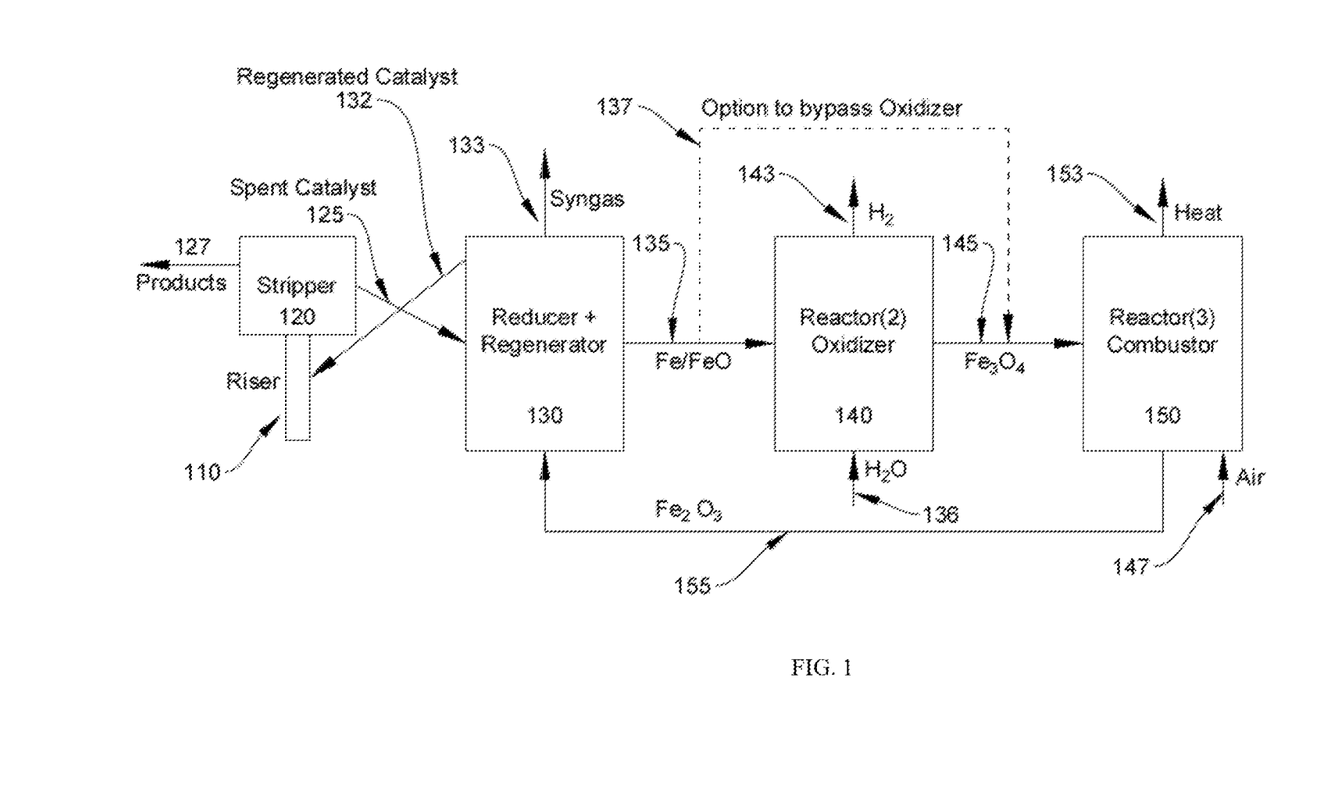
FIG. 1 is a schematic flow diagram of a CO maximization process by utilizing a chemical looping process in a FCC process.

The following reactions summarize the chemistry of each reactor of the Chemical Looping process. Reactions in the three reactors are as follows:

The Reducer-Regenerator Reactor: $Fe_2O_3 + C_xH_yO_z$ (catalyst coke) → $Fe/FeO + CO + H_2$ The Oxidizer Reactor: $Fe/FeO + H_2O → Fe_3O_4 + H_2$ The Combustor Reactor: $Fe_3O_4 + Air → Fe_2O_3 + Heat$ The new syngas generation process from an FCC unit is schematically illustrated using an example shown in FIG. 1. In FIG. 1, the FCC process is coupled with the Chemical Looping process by combining the Reducer of Chemical Looping process and Regenerator of FCC process. In the FCC process, crude oil is preheated to a temperature of about 315 to 430° C., fed into the riser 110 and then into the FCC reactor where it is brought into contact with a catalyst to break down or "crack" the high molecular weight hydrocarbons of the crude oil. After the catalytic cracking occurs, the catalyst particles are separated from the cracked vapors in the stripper 120. The spent catalyst particles 125 are fed into the Reducer-Regenerator 130.

Two process cycles occur in the present invention, the Chemical Looping process and the Fluid Catalytic Cracking process. The Chemical Looping process cycles metal oxides, such as iron-based oxygen carriers thru three reactors, i.e. a Reducer-Regenerator 130, an Oxidizer 140, and a Combustor 150. The FCC process cycles catalysts thru the Riser 110, the Stripper 120 and the Reducer-Regenerator reactor 130.

The function of Reducer-Regenerator reactor 130 is critical, as it is designed to convert the cokes on the spent FCC catalysts for syngas generation by metal oxides and the catalyst regeneration. The oxygen of the metal oxide particles is responsible for providing the necessary oxygen to the cokes on the spent catalysts for the reaction. As the metal oxides (such as iron oxide) provide a source of oxygen for the oxidation reaction of coke in the Reducer-Regenerator reactor 130, the metal oxides are reduced to a lower oxidation states (such FeO and Fe in the case of iron oxide). The iron oxides at a lower oxidation state have the potential to generate $H_2$ 143 and heat 153, when they are re-generated back to its original oxidation state. The $H_2$ and heat can be used in the refinery.

With respect to the chemical looping process, the metal oxide particles 155 (such as iron oxide) directly react with the spent FCC catalyst particles 125 to generate a $CO/H_2$ stream 133 in Reducer/Regenerator reactor 130. The Reducer/Regenerator reactor 130, the first reactor of the chemical loop, features a unique design of a gas-solid co-current moving bed configuration to achieve the reduction of metal oxide (such as $Fe_2O_3$) particles to lower its lower oxidation state (such as Fe and FeO), while fully converting the carbonaceous coke into synthesis gas 133, which can be utilized in downstream applications. In the second reactor 140, called the Oxidizer, the reduced iron particles 135 react with steam 136 to produce high purity $H_2$ 143. Because there are no other gas species involved in this reactor, the high purity $H_2$ 143 can be obtained without additional gas separation processes. In the last reactor, the Combustor 150, iron particles 145 are fully oxidized back to $Fe_2O_3$ 155 by air 147. This oxidation reaction of iron in the Combustor is highly exothermic reaction and the heat 153 can be recovered. Depending on the demand of the products, $H_2$ 143 and heat 153 from the Chemical Looping process, the operability of the oxidizer 140 and the combustor 150 can be adjusted.

In one embodiment, a method for producing synthesis gas from catalyst coke generated from a fluid catalytic cracking process is described comprising the following steps:

a) providing a chemical looping system comprising a reducer/regenerator reactor, an oxidizer reactor and a combustor reactor;

b) feeding catalyst coke particles and metal oxide particles into the reducer/regenerator reactor of the chemical looping system to produce a plurality of streams comprising a regenerated catalyst stream, a synthesis gas stream and a reduced metal oxide particle stream;

c) feeding the stream of reduced metal oxide particles and a stream of water vapor into the oxidizer reactor of the chemical looping system to produce a plurality of streams comprising a hydrogen stream and a stream of oxidized metal oxide particles; and d) feeding the stream of oxidized metal oxide particles and a stream of air into the combustor reactor of the chemical looping system to produce heat and a stream of metal oxide particles. In another embodiment, the metal oxide particles are selected from the group consisting of copper oxide, nickel oxide, magnesium oxide, iron oxide, manganese oxide and mixtures thereof.

In a further embodiment, the metal oxide particles comprise iron oxide. In a further embodiment, the iron oxide is $Fe_2O_3$. In a further embodiment, the reduced metal oxide particles comprise iron and iron oxide particles. In a further embodiment, the iron oxide is FeO. In another embodiment, the oxidized metal oxide particles comprise $Fe_3O_4$.

In another embodiment, the synthesis gas stream comprises greater that 60 vol % carbon monoxide.

In another embodiment, the catalyst coke particles are fed into a single stage reactor.

In another embodiment, when the metal oxide is $Fe_2O_3$, the molar ratio of the metal oxide particles to catalyst coke particles is about 1.4:1 to about 0.8:1. In a further embodiment, when the metal oxide is $Fe_2O_3$, the molar ratio of the metal oxide particles to catalyst coke is about 1.2:1 to about 0.8:1. In a further embodiment, when the metal oxide is $Fe_2O_3$, the molar ratio of the metal oxide particles to catalyst coke is about 1:1.

In another embodiment, the temperature of the reducer/regenerator reactor is about 500 to 1000° C.

In another embodiment, wherein the synthesis gas stream contains substantially no nitrogen.

In another embodiment, a reducer/regenerator reactor for a fluid catalytic process comprises a chemical looping system to produce synthesis gas.

Generally, the Chemical Looping process is known as a $CO_2$ capture process that utilizes the metal oxide particle as oxygen carriers. The conventional means of the Chemical Looping process is to capture $CO_2$ from the carbonaceous fuels by taking advantage of unique thermodynamic equilibrium of metal oxides. However, the operation conditions of Chemical Looping process in this invention are proposed in the different regions of thermodynamic equilibrium of metal oxides to generate the CO containing syngas instead of pure $CO_2$. For the generation of syngas from this process, the Reducer-Regenerator unit employs the iron oxides and is designed as a fluidized bed reactor as in FIG. 2a or co-current moving bed reactor as shown in FIG. 2b.

Fluidized Bed Reducer/Regenerator Reactor

Figure 2A:
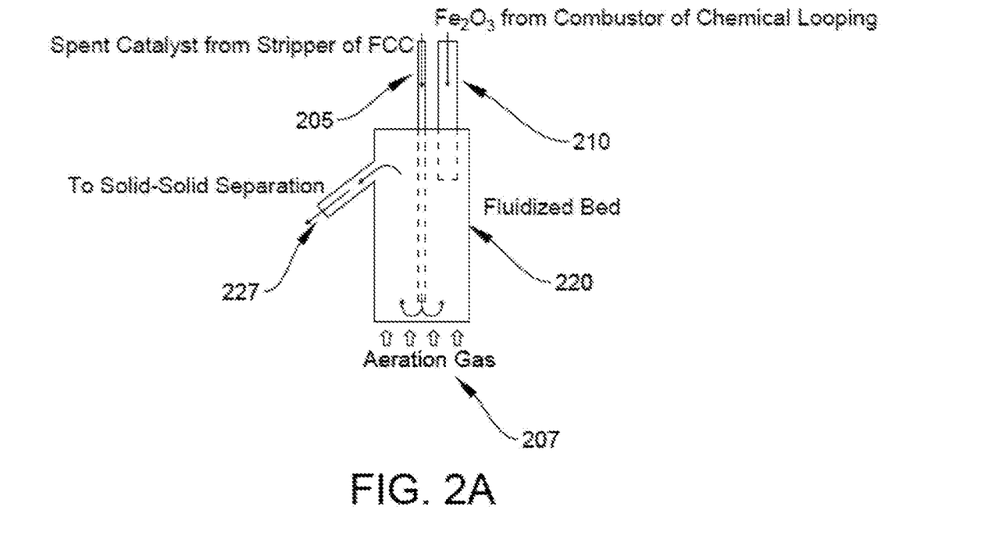
FIG. 2 is a diagram of (a) a fluidized bed reactor and (b) a co-current moving bed reactor.
Figure 2B:
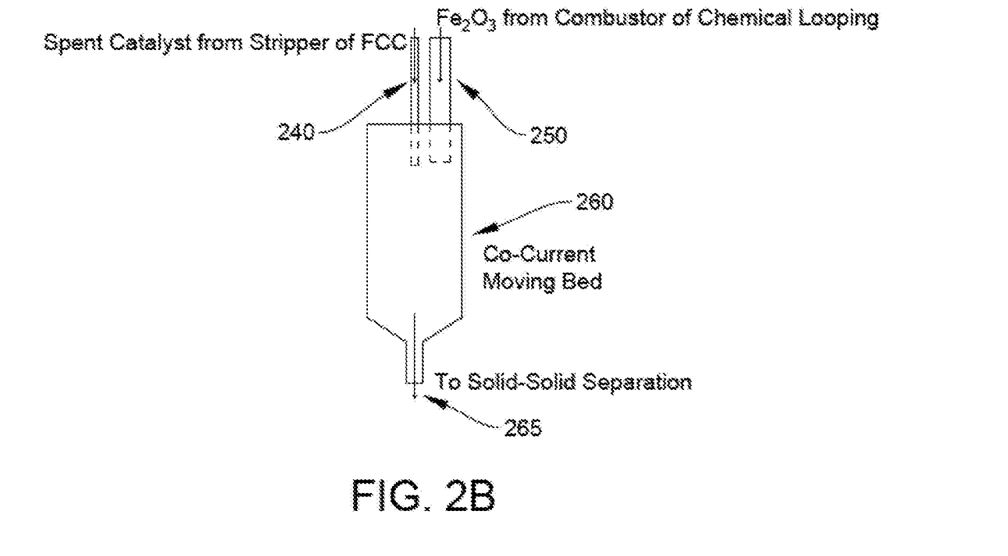

The generation of synthesis gas utilizing a fluidized bed Reducer/Regenerator reactor is schematically illustrated in FIG. 2a. In one embodiment, the Reducer/Regenerator reactor is optionally configured as a co-current fluidized bed 220, where large-sized metal oxide particles 210 (such as iron oxide) are packed and slowly move downward and the spent FCC catalyst particles 205 are fluidized between the large-sized metal oxide particles to flow in the same direction as the metal oxide particles. To maintain fluidized bed conditions, the gas velocity in the fluidized bed reactor 220 is maintained higher than the minimum fluidization velocity. The total gas velocity of the fluidized bed reactor 220 comprises the velocity of the aeration gas 207 and the velocity of the evolving synthesis gas from the reaction between the metal oxide particles 210 and the catalyst coke particles 205. As shown in FIG. 2a, the metal oxide particles 210 and the spent FCC catalyst particles 205 flow in the same direction downward in the fluidized bed Reducer/Regenerator reactor 220. The aeration gas 207, however, flows upward, in the opposite direction of the metal oxide particles 210 and the spent FCC catalyst particles 205.

Preferably, when the synthesis gas has started evolving from the reaction between the metal oxide particles 210 and the catalyst coke particles 205, the aeration gas 207 is a portion of the evolved synthesis gas from the fluidized bed reactor 220.

Both the metal oxide particles and the spent catalyst coke particles are well mixed in the fluidized bed reactor, while generating syngas that contains high concentrations of CO and $H_2$. As the spent catalysts flow with the iron oxide particles, the coke particles on the FCC catalyst are directly converted to CO and $H_2$ by the iron oxide particles. After the coke conversion in the reactor 220, the catalyst particles are separated from the reduced metal oxide particles thru a solid-solid separation step 227. Effective separation of the catalyst particles from the iron particles is preferred, because the leakage of iron particles may result in catalyst fouling and affect the yield and quality of the FCC unit. The large particle size difference between the FCC catalyst particles and the iron-based oxygen particles enables the separation of the two solid particles. Physical sieves may be applied for the solid-solid separation.

In the operation of Reducer/Regenerator reactor 220, it is important to regulate the vertical profile of gas velocity throughout the Reducer/Regenerator reactor 220. In order to keep the fluidized bed and fluidizing configurations for the iron particles and the FCC catalyst particles, respectively, the gas velocity is maintained higher than the minimum fluidization velocity of the metal oxide carriers. The large particle size difference between these two particle streams provides a large operation window in terms of gas velocity management. In estimating the gas velocity the evolved CO throughout the reactor needs to be taken into account as the catalyst coke is converted to CO by the metal oxide oxygen carrier. Depending on the demands from the refinery, the reduced iron particles from the Reducer/Regenerator Reactor have the option to generate heat or $H_2$ in their respective reactors.

In another embodiment, a method for producing synthesis gas from catalyst coke generated from a fluid catalytic cracking process is described comprising the following steps:
  a) providing a chemical looping system comprising a fluidized bed reducer/regenerator reactor, an oxidizer reactor and a combustor reactor;
  b) feeding aeration gas, catalyst coke particles and metal oxide particles into the fluidized bed reducer/regenerator reactor of the chemical looping system to produce a plurality of streams comprising a regenerated catalyst stream, a synthesis gas stream and a reduced metal oxide particle stream;
  c) feeding the stream of reduced metal oxide particles and a stream of water vapor into the oxidizer reactor of the chemical looping system to produce a plurality of streams comprising a hydrogen stream and a stream of oxidized metal oxide particles; and
  d) feeding the stream of oxidized metal oxide particles and a stream of air into the combustor reactor of the chemical looping system to produce heat and a stream of metal oxide particles. In another embodiment, the metal oxide particles are selected from the group consisting of copper oxide, nickel oxide, magnesium oxide, iron oxide, manganese oxide and mixtures thereof.

In a further embodiment, the reduced metal oxide particle stream and the regenerated catalyst stream of the fluidized bed reactor flow in the same direction. In another embodiment, the aeration gas stream of the fluidized bed reactor flows in the opposite direction of the reduced metal oxide particle stream and the regenerated catalyst stream.

In another embodiment, the aeration gas of the fluidized bed reactor is a portion of the evolved synthesis gas from the fluidized bed reactor.

In another embodiment, wherein the velocity of the catalyst coke particles stream in the fluidized bed reactor is higher than the minimum fluidization velocity of the reduced metal oxide particle stream.

In a further embodiment, the metal oxide particles comprise iron oxide. In a further embodiment, the iron oxide is $Fe_2O_3$. In a further embodiment, the reduced metal oxide particles comprise iron and iron oxide particles. In a further embodiment, the iron oxide is FeO. In another embodiment, the oxidized metal oxide particles comprise $Fe_3O_4$.

In another embodiment, the synthesis gas stream comprises greater that 60 vol % carbon monoxide.

In another embodiment, the catalyst coke particles are fed into a single stage reactor.

In another embodiment, when the metal oxide is $Fe_2O_3$, the molar ratio of the metal oxide particles to catalyst coke particles is about 1.4:1 to about 0.8:1. In a further embodiment, when the metal oxide is $Fe_2O_3$, the molar ratio of the metal oxide particles to catalyst coke is about 1.2:1 to about 0.8:1. In a further embodiment, when the metal oxide is $Fe_2O_3$, the molar ratio of the metal oxide particles to catalyst coke is about 1:1.

In another embodiment, the temperature of the fluidized bed reducer/regenerator reactor is less than 1000° C. In a further embodiment, the temperature of the fluidized bed reducer/regenerator reactor is less than 980° C. In a further embodiment, the temperature of the fluidized bed reducer/regenerator reactor is less than 950° C. In a further embodiment, the temperature of the fluidized bed reducer/regenerator reactor is less than 900° C.

In another embodiment, the temperature of the fluidized bed reducer/regenerator reactor is about 500 to 1000° C. In another embodiment, the temperature of the fluidized bed reducer/regenerator reactor is about 500 to 980° C. In another embodiment, the temperature of the fluidized bed reducer/regenerator reactor is about 500 to 950° C. In another embodiment, the temperature of the fluidized bed reducer/regenerator reactor is about 500 to 900° C.

In a further embodiment, the synthesis gas stream contains substantially no nitrogen.

In another embodiment, a fluidized bed reducer/regenerator reactor for a fluid catalytic process comprises a chemical looping system to produce synthesis gas. In a further embodiment, the chemical looping system of the fluidized bed reducer/regenerator reactor comprises:
  a) a fluidized bed reducer/regenerator reactor, an oxidizer reactor and a combustor reactor;

b) feeding aeration gas, catalyst coke particles and metal oxide particles into the fluidized bed reducer/regenerator reactor of the chemical looping system to produce a plurality of streams comprising a regenerated catalyst stream, a synthesis gas stream and a reduced metal oxide particle stream;

c) feeding the stream of reduced metal oxide particles and a stream of water vapor into the oxidizer reactor of the chemical looping system to produce a plurality of streams comprising a hydrogen stream and a stream of oxidized metal oxide particles; and d) feeding the stream of oxidized metal oxide particles and a stream of air into the combustor reactor of the chemical looping system to produce heat and a stream of metal oxide particles.

Moving Bed Reducer/Regenerator Reactor

The generation of synthesis gas utilizing a co-current moving bed Reducer/Regenerator reactor is schematically illustrated in FIG. 2b. In another embodiment, the Reducer/Regenerator reactor 260 is configured as a co-current moving bed, where large-sized iron metal oxide particles 250 are packed and the spent FCC catalyst particles 240 flow downward in the same direction as the metal oxide particles. In the co-current flow moving bed set-up, the gas velocity is maintained below the minimum fluidization velocity of iron particles, in order to maintain the packed-moving bed configuration. The co-current moving bed allows the iron particles and the spent catalyst particles to flow in the same direction.

In a further embodiment, the co-current moving bed is the preferred embodiment of the Reducer/Regenerator reactor.

In another embodiment, a method for producing synthesis gas from catalyst coke generated from a fluid catalytic cracking process is described comprising the following steps:

a) providing a chemical looping system comprising a co-current moving bed reducer/regenerator reactor, an oxidizer reactor and a combustor reactor;

b) feeding catalyst coke particles and metal oxide particles into the co-current moving bed reducer/regenerator reactor of the chemical looping system to produce a plurality of streams comprising a regenerated catalyst stream, a synthesis gas stream and a reduced metal oxide particle stream;

c) feeding the stream of reduced metal oxide particles and a stream of water vapor into the oxidizer reactor of the chemical looping system to produce a plurality of streams comprising a hydrogen stream and a stream of oxidized metal oxide particles; and d) feeding the stream of oxidized metal oxide particles and a stream of air into the combustor reactor of the chemical looping system to produce heat and a stream of metal oxide particles. In another embodiment, the metal oxide particles are selected from the group consisting of copper oxide, nickel oxide, magnesium oxide, iron oxide, manganese oxide and mixtures thereof.

In a further embodiment, the reduced metal oxide particle stream and the regenerated catalyst stream of the co-current moving bed reactor flow in the same direction.

In another embodiment, wherein the velocity of the catalyst coke particles stream in the co-current moving bed reactor is lower than the minimum fluidization velocity of the reduced metal oxide particle stream.

In a further embodiment, the metal oxide particles comprise iron oxide. In a further embodiment, the iron oxide is $Fe_2O_3$. In a further embodiment, the reduced metal oxide particles comprise iron and iron oxide particles. In a further embodiment, the iron oxide is FeO. In another embodiment, the oxidized metal oxide particles comprise $Fe_3O_4$.

In another embodiment, the synthesis gas stream comprises greater that 60 vol % carbon monoxide.

In another embodiment, the catalyst coke particles are fed into a single stage reactor.

In another embodiment, when the metal oxide is $Fe_2O_3$, the molar ratio of the metal oxide particles to catalyst coke particles is about 1.4:1 to about 0.8:1. In a further embodiment, when the metal oxide is $Fe_2O_3$, the molar ratio of the metal oxide particles to catalyst coke is about 1.2:1 to about 0.8:1. In a further embodiment, when the metal oxide is $Fe_2O_3$, the molar ratio of the metal oxide particles to catalyst coke is about 1:1.

In another embodiment, the temperature of the co-current moving bed reducer/regenerator reactor is less than 1000° C. In a further embodiment, the temperature of the co-current moving bed reducer/regenerator reactor is less than 980° C. In a further embodiment, the temperature of the co-current moving bed reducer/regenerator reactor is less than 950° C. In a further embodiment, the temperature of the co-current moving bed reducer/regenerator reactor is less than 900° C.

In another embodiment, the temperature of the co-current moving bed reducer/regenerator reactor is about 500 to 1000° C. In another embodiment, the temperature of the co-current moving bed reducer/regenerator reactor is about 500 to 980° C. In another embodiment, the temperature of the co-current moving bed reducer/regenerator reactor is about 500 to 950° C. In another embodiment, the temperature of the co-current moving bed reducer/regenerator reactor is about 500 to 900° C.

In a further embodiment, the synthesis gas stream contains substantially no nitrogen.

In another embodiment, a co-current moving bed reducer/regenerator reactor for a fluid catalytic process comprises a chemical looping system to produce synthesis gas. In a further embodiment, the chemical looping system of the co-current moving bed reducer/regenerator reactor comprises:

a) a co-current moving bed reducer/regenerator reactor, an oxidizer reactor and a combustor reactor;

b) feeding catalyst coke particles and metal oxide particles into the co-current moving bed reducer/regenerator reactor of the chemical looping system to produce a plurality of streams comprising a regenerated catalyst stream, a synthesis gas stream and a reduced metal oxide particle stream;

c) feeding the stream of reduced metal oxide particles and a stream of water vapor into the oxidizer reactor of the chemical looping system to produce a plurality of streams comprising a hydrogen stream and a stream of oxidized metal oxide particles; and d) feeding the stream of oxidized metal oxide particles and a stream of air into the combustor reactor of the chemical looping system to produce heat and a stream of metal oxide particles.

Figure 3:
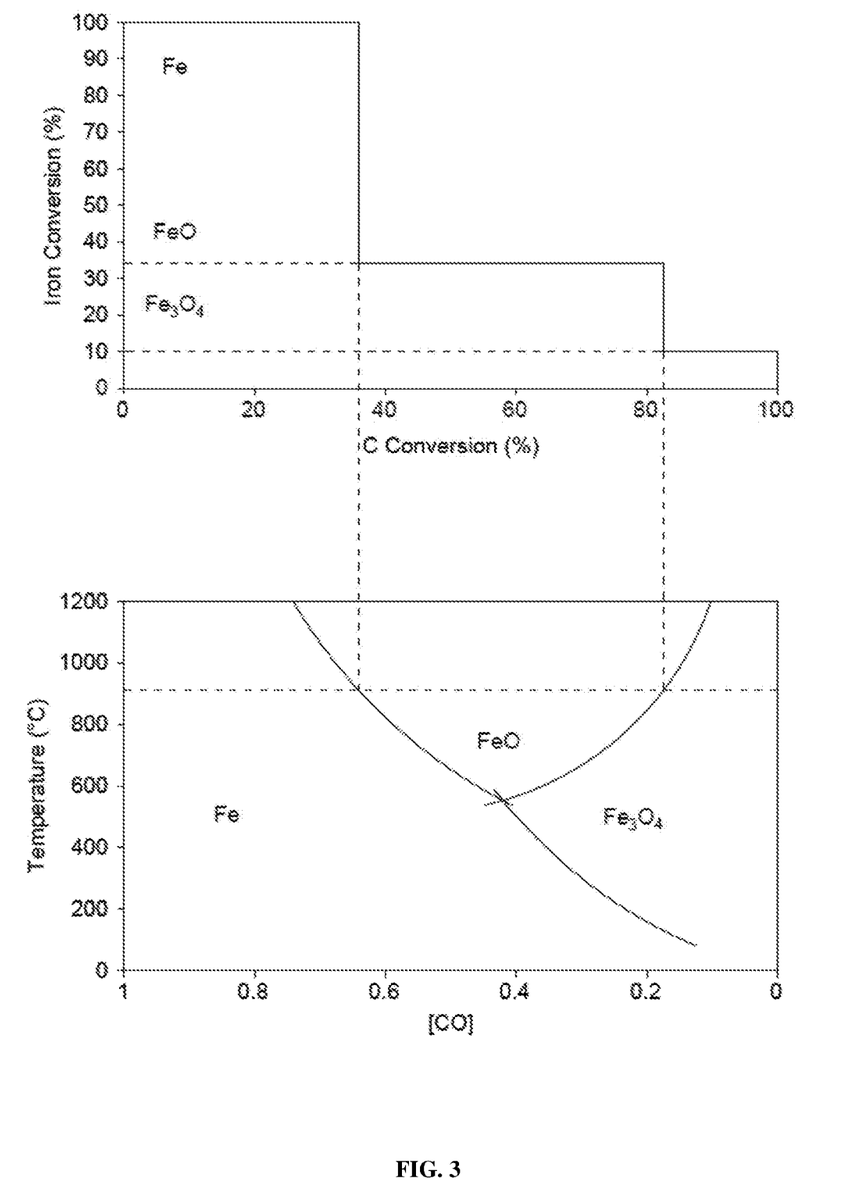
FIG. 3 is a diagram of an equilibrium line of iron-CO system (Solid line) and operating line of a fluidized bed or a co-current moving bed (dotted line).

FIG. 3 illustrates the equilibrium iron-gas system as a function of gas compositions and temperature. The equilibrium line of the iron-CO system is the solid line of FIG. 3 and the operating line of a fluidized bed or co-current moving bed Reducer-Regenerator is the dotted line.

In this thermodynamic equilibrium calculation, CO and $CO_2$ are considered as reducing and oxidizing gases, respectively. For example, when the metal oxide is FeO, the most favored form of iron oxide, the composition of CO is set at 50% and 900° C. At this condition, the thermodynamic equilibrium reduces $Fe_3O_4$ to FeO, and oxidizes Fe to FeO. If FeO needs to be further reduced to metallic iron, Fe, a) the temperature must be reduced at the same gas composition, moving the equilibrium system (as exemplified in FIG. 3) to the parallel left or b) the reducing gas, CO concentration must be increased to push the equilibrium upward. The operating line (dotted line) in FIG. 3 can be drawn on the phase diagram of iron. For the high concentration of CO in the product gas at 900° C., the fluidized bed or the co-current moving bed system reduces the $Fe_2O_3$ to FeO, while producing 36% $CO_2$ and 64% CO. In summary, the thermodynamic equilibrium shows that the concentrations of resulting gas in the Reducer-Regenerator reactor strongly depend on the oxidation states of iron oxide particles. For example, a higher concentration of CO is projected with more FeO and Fe presence.

Figure 4:
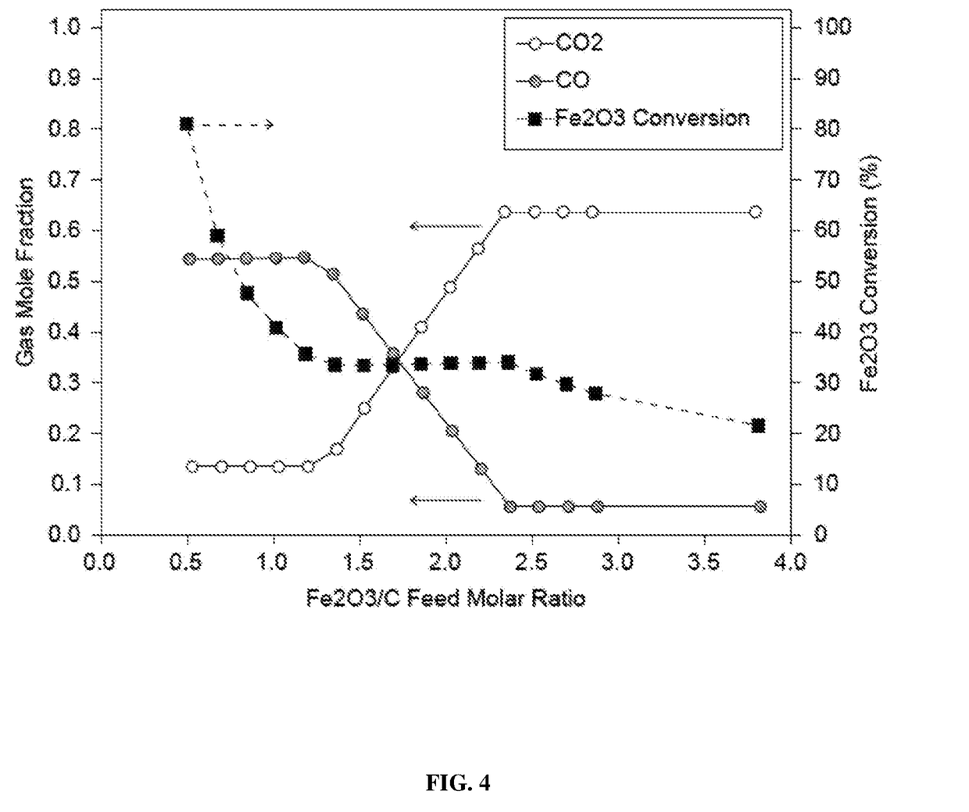
FIG. 4 is a thermodynamic calculation for CO and $CO_2$ concentration of the present invention.

FIG. 4 illustrates the results of a thermodynamic simulation of CO and $CO_2$ concentrations as a function of $Fe_2O_3/C$ feed molar ratio in a fluidized bed or co-current moving bed. On the left-hand y-axis of FIG. 4 is the gas mole fraction of either $CO_2$ (open circles) or CO (closed circles). On the right-hand y-axis of FIG. 4 is the $Fe_2O_3$ conversion in percent (closed squares). On the x-axis of FIG. 4 is the $Fe_2O_3/C$ feed molar ratio. Here, C in the $Fe_2O_3/C$ feed molar ratio, represents the cokes in the spent catalyst. Based on the thermodynamic estimation in FIG. 4, the CO concentration and iron oxide conversion are optimized, when the $Fe_2O_3/C$ feed molar ratio is around 1. When the $Fe_2O_3/C$ ratio is at 1.18, the concentrations of CO and $CO_2$ are 0.5451 and 0.1369, respectively, with approximately 35.62% iron oxide conversion, which corresponds to a mostly FeO state. The reduced iron particles undergo to a series of reactions in Oxidizer and Combustor, in order to generate valuable products, $H_2$ and heat, respectively. As the iron particles complete the cycles at Combustor, the iron particles are fully regenerated back to $Fe_2O_3$ and loop back to the Reducer-Regenerator for additional cycles.

Applications of Syngas in Downstream
Production of Alcohol

This highly concentrated syngas can be utilized in many applications. Exemplary uses of synthesis gas are syngas fermentation for alcohol production, hydrogen production and synthesis of chemical intermediates. One example is a bio-based syngas fermentation process to produce alcohols such as ethanol. The syngas from Chemical Looping process has the potential to improve the efficiency of bio-based fermentation process by enhancing the mass transfer of syngas into liquid phase, as the syngas contains no $N_2$ unlike other syngas from conventional sources such as biomass and coal gasification. The syngas fermentation generates highly concentrated $CO_2$ stream as a flue gas, which can be readily available for sequestration without major separation processes. Reactions of syngas fermentation for the production of alcohols, such as ethanol, are summarized below.

In one embodiment, the method for producing synthesis gas from catalyst coke generated from a fluid catalytic cracking process described in the present invention utilizes the synthesis gas to produce alcohol and $CO_2$.

In a further embodiment, the synthesis gas contains substantially no nitrogen.

In a further embodiment, the alcohol produced from the synthesis gas is a $C_{2-15}$ alcohol. In a further embodiment, the $C_{2-15}$ alcohol is ethanol.

In a further embodiment, the $CO_2$ produced from the synthesis gas is sequestered.

Production of $H_2$ and $CO_2$

In another example, the method for producing synthesis gas from catalyst coke generated from a fluid catalytic cracking process described in the present invention utilizes the synthesis gas to produce $H_2$ and $CO_2$ via a water-gas shift reaction. In the water-gas shift reaction, carbon monoxide and water vapor react to form carbon dioxide and hydrogen:

In one embodiment, the method for producing synthesis gas from catalyst coke generated from a fluid catalytic cracking process described in the present invention utilizes the synthesis gas to produce $CO_2$ and $H_2$.

In a further embodiment, the synthesis gas contains substantially no nitrogen. In a further embodiment, the $H_2$ and $CO_2$ produced from the synthesis gas are separated by physical absorption process. In a further embodiment, the $CO_2$ produced from the synthesis gas is sequestered.

Additional Embodiments

This disclosure may further include one or more of the following non-limiting embodiments:

E1. A method for producing synthesis gas from catalyst coke generated from a fluid catalytic cracking process comprising the following steps:
  a) providing a chemical looping system comprising a fluidized bed reducer/regenerator reactor, an oxidizer reactor and a combustor reactor;
  b) feeding aeration gas, catalyst coke particles and metal oxide particles into the fluidized bed reducer/regenerator reactor of the chemical looping system to produce a plurality of streams comprising a regenerated catalyst stream, a synthesis gas stream and a reduced metal oxide particle stream;
  c) feeding the stream of reduced metal oxide particles and a stream of water vapor into the oxidizer reactor of the chemical looping system to produce a plurality of streams comprising a hydrogen stream and a stream of oxidized metal oxide particles; and
  d) feeding the stream of oxidized metal oxide particles and a stream of air into the combustor reactor of the chemical looping system to produce heat and a stream of metal oxide particles.

E2. A method for producing synthesis gas from catalyst coke generated from a fluid catalytic cracking process comprising the following steps:
  a) providing a chemical looping system comprising a co-current moving bed reducer/regenerator reactor, an oxidizer reactor and a combustor reactor;
  b) feeding catalyst coke particles and metal oxide particles into the co-current moving bed reducer/regenerator reactor of the chemical looping system to produce a plurality of streams comprising a regenerated catalyst stream, a synthesis gas stream and a reduced metal oxide particle stream;
  c) feeding the stream of reduced metal oxide particles and a stream of water vapor into the oxidizer reactor of the chemical looping system to produce a plurality of streams comprising a hydrogen stream and a stream of oxidized metal oxide particles; and
  d) feeding the stream of oxidized metal oxide particles and a stream of air into the combustor reactor of the chemical looping system to produce heat and a stream of metal oxide particles.

E3. A method for producing synthesis gas of E1 or E2, wherein the metal oxide particles are selected from the group consisting of copper oxide, nickel oxide, magnesium oxide, iron oxide, manganese oxide and mixtures thereof.

E4. The method of E3, wherein the metal oxide particles comprise iron oxide.

E5. The method of E4, wherein the iron oxide is $Fe_2O_3$.

E6. The method of E1 or E2, wherein the reduced metal oxide particles comprise iron and iron oxide particles.

E7. The method of E6, wherein the iron oxide is FeO.

E8. The method of E1 or E2, wherein the oxidized metal oxide particles comprise $Fe_3O_4$.

E9. The method of E1 or E2, wherein the reducer/regenerator reactor has a temperature of less than 1000° C.

E10. The method of E10, wherein the temperature of the reducer/regenerator reactor is less than 980° C.

E11. The method of E10, wherein the temperature of the reducer/regenerator reactor is less than 950° C.

E12. The method of E11, wherein the temperature of the reducer/regenerator reactor is less than 900° C.

E13. The method of E1 or E2, wherein the reducer/regenerator reactor has a temperature of about 500 to 1000° C.

E14. The method of E13, wherein the temperature of the reducer/regenerator reactor is about 500 to 980° C.

E15. The method of E14, wherein the temperature of the reducer/regenerator reactor is about 500 to 950° C.

E16. The method of E15, wherein the temperature of the reducer/regenerator reactor is about 500 to 900° C.

E17. The method of E1 or E2, wherein the catalyst coke particles are fed into a single stage reactor.

E18. A reducer/regenerator reactor for a fluid catalytic process comprises a chemical looping system to produce synthesis gas.

E19. The reducer/regenerator reactor of E18, wherein the reducer/regenerator reactor is a fluidized bed.

E20. The reducer/regenerator reactor of E18, wherein the reducer/regenerator reactor is a co-current moving bed.

E21. The chemical looping system of the fluidized bed reducer/regenerator reactor of E19 comprising:
  a) a fluidized bed reducer/regenerator reactor, an oxidizer reactor and a combustor reactor;
  b) feeding aeration gas, catalyst coke particles and metal oxide particles into the fluidized bed reducer/regenerator reactor of the chemical looping system to produce a plurality of streams comprising a regenerated catalyst stream, a synthesis gas stream and a reduced metal oxide particle stream;
  c) feeding the stream of reduced metal oxide particles and a stream of water vapor into the oxidizer reactor of the chemical looping system to produce a plurality of streams comprising a hydrogen stream and a stream of oxidized metal oxide particles; and
  d) feeding the stream of oxidized metal oxide particles and a stream of air into the combustor reactor of the chemical looping system to produce heat and a stream of metal oxide particles.

E22. The chemical looping system of the co-current moving bed reducer/regenerator reactor of E20 comprising:
  a) a co-current moving bed reducer/regenerator reactor, an oxidizer reactor and a combustor reactor;
  b) feeding catalyst coke particles and metal oxide particles into the co-current moving bed reducer/regenerator reactor of the chemical looping system to produce a plurality of streams comprising a regenerated catalyst stream, a synthesis gas stream and a reduced metal oxide particle stream;
  c) feeding the stream of reduced metal oxide particles and a stream of water vapor into the oxidizer reactor of the chemical looping system to produce a plurality of streams comprising a hydrogen stream and a stream of oxidized metal oxide particles; and
  d) feeding the stream of oxidized metal oxide particles and a stream of air into the combustor reactor of the chemical looping system to produce heat and a stream of metal oxide particles.

In the specification and in the claims, the terms "including" and "comprising" are open-ended terms and should be interpreted to mean "including, but not limited to". These terms encompass the more restrictive terms "consisting essentially of" and "consisting of." It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", "characterized by" and "having" can be used interchangeably.

All documents described herein are incorporated by reference herein, including any priority documents and/or testing procedures to the extent they are not inconsistent with this text. As is apparent from the foregoing general description and the specific embodiments, while forms of the present disclosure have been illustrated and described, various modifications can be made without departing from the spirit and scope of the present disclosure. Accordingly, it is not intended that the present disclosure be limited thereby.

The various descriptive elements and numerical ranges disclosed herein for the reactants used to make petroleum distillate products, and their use can be combined with other descriptive elements and numerical ranges to describe the invention(s); further, for a given element, any upper numerical limit can be combined with any lower numerical limit described herein. The features of the invention are described in the following non-limiting examples.

The invention claimed is:

1. A method for producing synthesis gas from catalyst coke generated from a fluid catalytic cracking process by
  a) providing a chemical looping system comprising a combined reducer-regenerator reactor, an oxidizer reactor and a combustor reactor;
  b) feeding catalyst coke particles and metal oxide particles into the reducer/regenerator reactor of the chemical looping system to produce a plurality of streams comprising a regenerated catalyst stream, a synthesis gas stream and a reduced metal oxide particle stream;
  c) feeding the stream of reduced metal oxide particles and a stream of water vapor into the oxidizer reactor of the chemical looping system to produce a plurality of streams comprising a hydrogen stream and a stream of oxidized metal oxide particles; and
  d) feeding the stream of oxidized metal oxide particles and a stream of air into the combustor reactor of the chemical looping system to produce heat and a stream of metal oxide particles.

2. The method of claim 1, wherein the combined reducer-regenerator reactor is a moving bed reactor.

3. The method of claim 2, wherein the reduced metal oxide particle stream and the regenerated catalyst stream of the moving bed reactor flow in the same direction.

4. The method of claim 1, wherein the combined reducer-regenerator reactor is a fluidized bed reactor.

5. The method of claim 4, wherein the reduced metal oxide particle stream and the regenerated catalyst stream of the fluidized bed reactor flow in the same direction.

6. The method of claim 2, wherein the velocity of the catalyst coke particles stream is below the minimum fluidization velocity of the reduced metal oxide particle stream.

7. The method of claim 4, wherein the velocity of the catalyst coke particles stream in the fluidized bed reactor is higher than the minimum fluidization velocity of the reduced metal oxide particle stream.

8. The method of claim 1, wherein the metal oxide particles are selected from the group consisting of copper oxide, nickel oxide, magnesium oxide, iron oxide, manganese oxide and mixtures thereof.

9. The method of claim 8, wherein the metal oxide particles comprise iron oxide.

10. The method of claim 9, wherein the iron oxide is $Fe_2O_3$.

11. The method of claim 1, wherein the reduced metal oxide particles comprise iron and iron oxide particles.

12. The method of claim 11, wherein the iron oxide is FeO.

13. The method of claim 1, wherein the oxidized metal oxide particles comprise $Fe_3O_4$.

14. The method of claim 1, wherein the synthesis gas stream comprises greater that 60 vol % carbon monoxide.

15. The method of claim 1, wherein the catalyst coke particles are fed into a single stage reactor.

16. The method of claim 1, wherein the synthesis gas is used to produce alcohol and $CO_2$.

17. The method of claim 16, wherein the alcohol is a $C_{2-15}$ alcohol.

18. The method of claim 17, wherein the $C_{2-15}$ alcohol is ethanol.

19. The method of claim 1, wherein the synthesis gas is used to produce $H_2$ and $CO_2$ via a water-gas shift reaction.

20. The method of claim 19, wherein the $H_2$ and $CO_2$ products are separated by physical absorption process.

21. The method of claim 16 or 19, wherein the $CO_2$ is sequestered.

22. The method of claim 10, wherein the molar ratio of the metal oxide particles to catalyst coke particles is about 1.4:1 to about 0.8:1.

23. The method of claim 22, wherein the molar ratio of the metal oxide particles to catalyst coke is about 1:1.

24. The method of claim 1, wherein the temperature of the combined reducer-regenerator reactor is about 500 to 1000° C.

* * * * *